US00PP36484P3

(12) United States Plant Patent
Olesen

(10) Patent No.: US PP36,484 P3
(45) Date of Patent: Feb. 25, 2025

(54) ROSE PLANT NAMED "POULPAL102"

(50) Latin Name: *Rosa hybrida*
Varietal Denomination: Poulpal102

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,472

(22) Filed: Sep. 8, 2023

(65) Prior Publication Data

US 2024/0107911 P1 Mar. 28, 2024

(30) Foreign Application Priority Data

Sep. 30, 2022 (QZ) ..... PBR 2022/2170

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
CPC ..... A01H 6/749; A01H 5/02
See application file for complete search history.

*Primary Examiner* — Keith O. Robinson

(57) ABSTRACT

A new garden rose plant of the compact floribunda class which has abundant, yellow flowers and attractive foliage. This new and distinct variety has shown to be uniform and stable in the resulting generations from asexual propagation.

2 Drawing Sheets

Botanical designation: *Rosa hybrida.*
Variety denomination:
'Poulpal102'.

This application claims priority to Plant Breeder's Rights Application Number 2022/2170, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpal102', originated as a single seedling from the stated cross.

The new variety may be distinguished from its male pollen parent and female seed parent primarily by the following characteristics. The male pollen parent plant has flowers with a general tonality of Yellow Group 13A & 13B flowers while the general tonality of flowers on the newly claimed plant are Yellow Group 7A. The female seed parent plant grows to a height of 25 cm while the new variety grows to a height of 54 cm.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpal102' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpal102' was selected in the spring of 2015 by the inventor as a single plant from the progeny of the aforementioned hybridization.

Asexual reproduction of 'Poulpal102' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpal102' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal102'.

Specifically illustrated in FIG. 1 of the drawings are open flowers viewed from above and the side, flower petals detached revealing reproductive flower parts, sepals detached, flower bud and partially opened flower.

Figure 1:
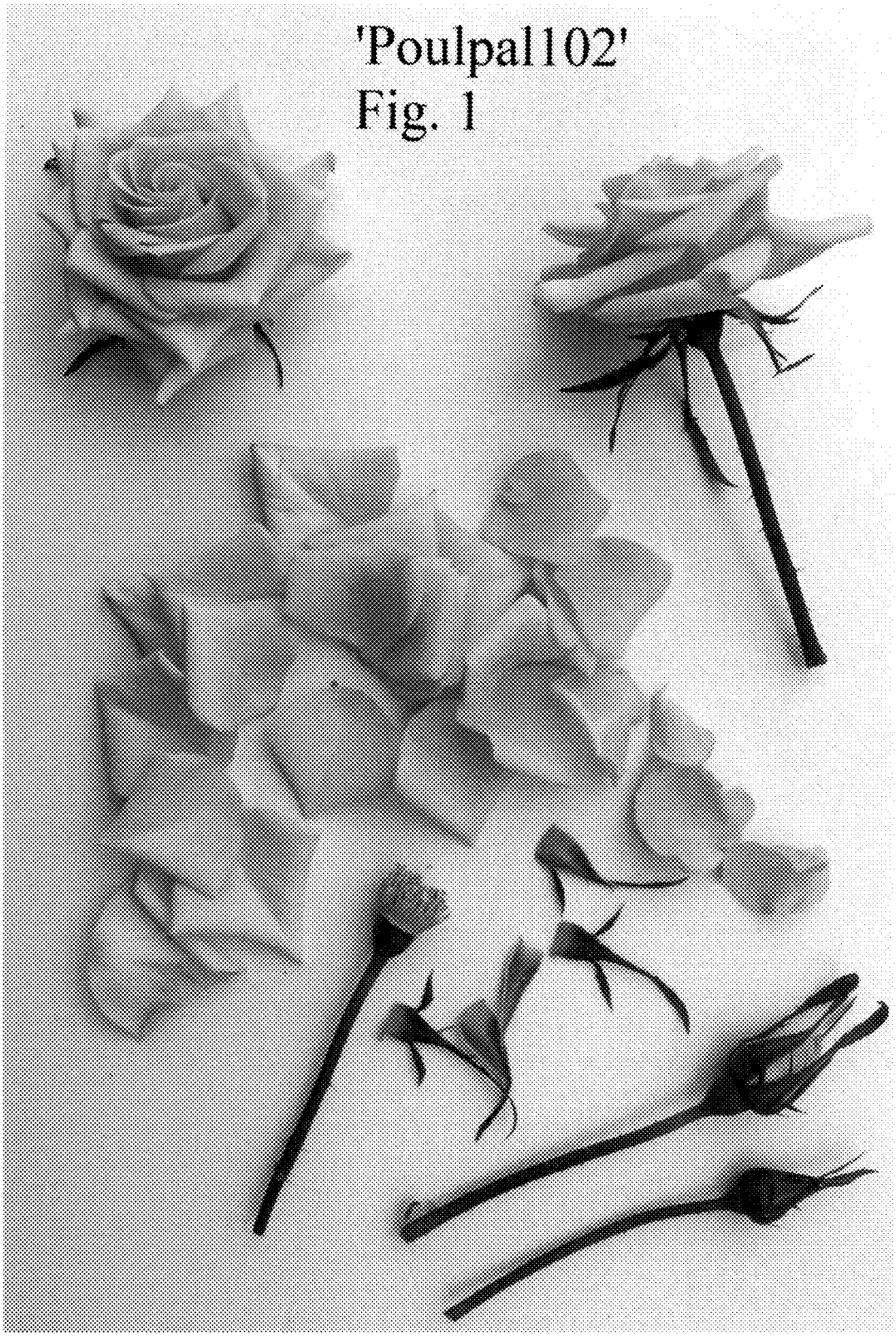
Figure 2:
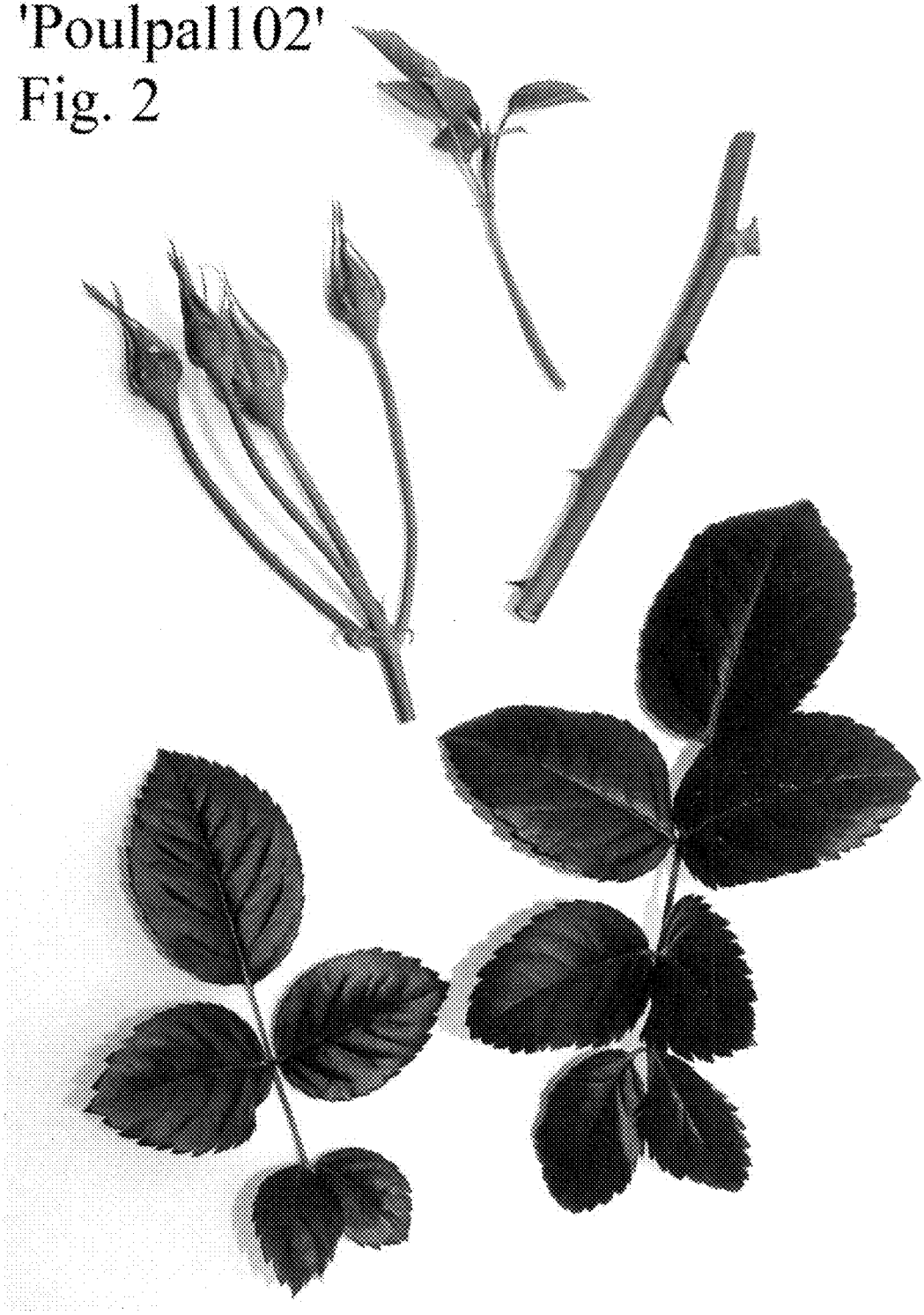

Specifically illustrated in FIG. 2 of the drawings are a cluster of flower buds on the branch, bare stem exhibiting prickles, juvenile growth, and mature leaves. Plants shown are 4 months old.

DETAILED DESCRIPTION OF THE VARIETY

The following is a description of 'Poulpal102', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpal074', U.S. Plant Pat. No. 31,633 are compared to the claimed plant. While 'Poulpal102' has about 28 flower petals, 'Poulpal074' has 40 flower petals. The claimed plant has a flower diameter of 65 mm while 'Poulpal074' has a flower diameter of 80 mm. Open flowers of 'Poulpal102' are generally Yellow Group 7A in color while 'Poulpal074' has a general tonality of Orange Group 24B.

FLOWER AND FLOWER BUD

Blooming habit: Continuous.

Flower bud:

- *Size.*—Upon opening, 26 mm in length from base of receptacle to end of bud. Bud diameter is 12 mm.
- *Bud form.*—Urceolate.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have strong foliaceous appendages on three of the five sepals.
- *Sepal size.*—35 mm long, 8 mm wide.
- *Receptacle.*—Texture: Smooth. Size: 9 mm in height, 10 mm wide. Color: Yellow-Green Group 144A. Shape: Campanulate.
- *Pedicel.*—Surface: Rough with many small soft prickles. Length: About 68 mm. Diameter: 2 mm on average. Color: Yellow-Green Group 144A. Strength: Strong.
- *Peduncle.*—Length: 2 to 6 cm. Diameter: About 3 mm. Color: Yellow-Green Group 144A. Texture: Smooth.

Flower bud development: Flower buds are borne single or in clusters of 3 to 5 flower buds per stem. Development as an umbel.

Flower bloom:

- *Fragrance.*—Moderate, floral, melon-like scent.
- *Duration.*—The blooms have a duration on the plant of approximately 21 days. Petals fall cleanly away from plant after flowers have fully matured.
- *Size.*—Flower diameter is about 65 mm when open. Flower depth is 26 mm.
- *Flower shape.*—Hybrid tea form, high centered with a high pointed center which is tightly closed.
- *Shape of flower, side view.*—The upper portion is convex. The lower portion is concave.

Petalage: Under normal conditions, flowers have about 28 petals.

General tonality of flower: Open flowers are Yellow Group 7A.

Petal color:

- *Upon opening, outer petals.*—Upper surface: Yellow Group 7A at the basal and middle zone. Marginal zone Yellow Group 8C. Lower surface: Yellow Group 8C marginal zone. Middle zone shades of Orange Group 29B. Basal zone Yellow Group 7A.
- *Upon opening, inner petals.*—Upper surface: Yellow Group 9A. Lower surface: Yellow Group 9A with shades of Orange Group 25C.
- *After opening, outer petals.*—Upper surface: Yellow Group 9B. Lower surface: Yellow Group 9A with shades of Orange Group 25C.
- *After opening, inner petals.*—Upper surface: Yellow Group 9B. Lower surface: Yellow Group 9A with shades of Orange Group 25C.

Petals:

- *Petal reflex.*—Strong bilateral.
- *Margin.*—Entire and uniform. Moderate undulations.
- *Shape.*—Broad and elliptic. Apex shape: Rounded. Base shape: Acute.
- *Size.*—About 37 mm (l)×39 mm (w).
- *Texture.*—Smooth.
- *Thickness.*—Average.

Petaloids:

- *Size.*—30 mm (l) by 25 mm (w).
- *Quantity.*—4 to 6.
- *Shape.*—Round.
- *Color.*—Upper surface Yellow Group 9B. Lower surface Yellow Group 9A with shades of Orange Group 25C.

Reproductive flower parts:

- *Pollen.*—None observed.
- *Anthers.*—Size: 2 mm in length. Color: Yellow Group 9D. Quantity: 48 on average.
- *Filaments.*—Color: Yellow Group 12A. Length: 9 mm.
- *Pistils.*—Length: 7 mm. Quantity: 33 on average.
- *Stigmas.*—Color: Greyed-Yellow Group 160B.
- *Styles.*—Color: Yellow-Green Group 145D.
- *Location of stigmas.*—Even in location relative to the length of the filaments and the height of the anthers.
- *Hips.*—None Observed.

PLANT

Plant growth: Upright. Plants are about 54 cm in height, and 37 cm wide.

Stems:

- *Color of juvenile growth.*—Yellow-Green Group 144A.
- *Color of mature growth.*—Yellow-Green Group 144A.
- *Length.*—Canes are about 27 cm from the base of the plant to the flowering portion.
- *Diameter.*—About 6 mm.
- *Internodes.*—On mature canes about 50 mm between nodes.
- *Surface texture.*—Young wood: Smooth. Older wood: Smooth.

Long prickles:

- *Incidence.*—About 5 prickles per 10 cm of stem.
- *Size.*—Average length of prickles on mature stems is 9 mm.
- *Shape.*—Upper portion is linear. Lower portion is deep concave.
- *Color.*—Juvenile prickles: Greyed-Purple Group 183A. Mature prickles: Greyed-Purple Group 183A.

Plant foliage:

- *Compound leaf.*—145 mm (l)×110 (w).
- *Quantity.*—2 leaves per 10 cm of stem on average.
- *Leaf bearing angle to the stem.*—75 to 90 degrees.

*Color of juvenile foliage*.—Upper side: Yellow-Green Group 144A with intonations of Greyed-Purple Group 183A at margins. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: About 10 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 21 mm. Diameter: 2 mm. Upper surface color: Yellow-Green Group 144A. Lower surface color: Yellow-Green Group 144A.

*Rachis*.—Length: About 45 mm. Upper surface color: Yellow-Green Group 144A. Lower surface color: Yellow-Green Group 144A.

*Leaflet*.—Quantity: Normally 5 or 7 leaflets. Margins: Serrated. Size: Terminal leaflets are about 75 mm long, 46 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpal102' substantially as described and illustrated herein.

* * * * *

'Poulpal102'

'Poulpal102'